United States Patent
Ogawa et al.

(10) Patent No.: US 11,324,461 B2
(45) Date of Patent: May 10, 2022

(54) X-RAY IMAGING APPARATUS

(71) Applicant: Shimadzu Corporation, Kyoto (JP)

(72) Inventors: Taku Ogawa, Kyoto (JP); Koki Yoshida, Kyoto (JP); Daisuke Murakami, Kyoto (JP); Dai Hirose, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 26 days.

(21) Appl. No.: 16/820,972

(22) Filed: Mar. 17, 2020

(65) Prior Publication Data

US 2020/0359977 A1 Nov. 19, 2020

(30) Foreign Application Priority Data

May 14, 2019 (JP) .............................. JP2019-091448

(51) Int. Cl.
*A61B 6/12* (2006.01)
*A61B 6/00* (2006.01)
*A61B 6/06* (2006.01)

(52) U.S. Cl.
CPC ............... *A61B 6/12* (2013.01); *A61B 6/06* (2013.01); *A61B 6/487* (2013.01); *A61B 6/58* (2013.01); *A61B 6/461* (2013.01); *A61B 6/469* (2013.01); *A61B 6/504* (2013.01); *A61B 6/5205* (2013.01)

(58) Field of Classification Search
CPC .. A61B 6/12; A61B 6/06; A61B 6/487; A61B 6/58; A61B 6/461; A61B 6/469; A61B 6/504
See application file for complete search history.

(56) References Cited

U.S. PATENT DOCUMENTS

| 2005/0002546 | A1 | 1/2005 | Florent et al. |
| 2008/0118023 | A1* | 5/2008 | Besson ................... A61B 6/12 378/8 |
| 2010/0104167 | A1 | 4/2010 | Sakaguchi et al. |
| 2013/0343631 | A1* | 12/2013 | Florent ................... A61B 6/12 382/132 |
| 2014/0051991 | A1 | 2/2014 | Sakaguchi et al. |
| 2016/0029989 | A1* | 2/2016 | Nagae ..................... A61B 6/12 378/42 |
| 2016/0361035 | A1* | 12/2016 | Lee ........................ A61B 6/545 |
| 2017/0065235 | A1 | 3/2017 | Sakaguchi et al. |
| 2018/0317865 | A1 | 11/2018 | Sakaguchi et al. |
| 2020/0000420 | A1 | 1/2020 | Sakaguchi et al. |

FOREIGN PATENT DOCUMENTS

| JP | 2005-510288 A | 4/2005 |
| JP | 2010-131371 A | 6/2016 |
| JP | 6115498 B2 | 4/2017 |

* cited by examiner

*Primary Examiner* — Chih-Cheng Kao
(74) *Attorney, Agent, or Firm* — Muir Patent Law, PLLC

(57) ABSTRACT

An X-ray imaging apparatus includes an X-ray irradiation region adjustment unit for adjusting an X-ray irradiation region and a control unit for controlling the X-ray irradiation region adjustment unit so as to adjust the X-ray irradiation region based on a set region of interest in the case of a region of interest highlighting mode that highlights a predetermined target object within the region of interest set in the image generated by the image processing unit.

9 Claims, 6 Drawing Sheets

X-RAY IMAGING APPARATUS

CROSS-REFERENCE TO RELATED APPLICATIONS

The related application number No JP2019-091448, entitled "X-ray imaging apparatus", filed on May 14, 2019, and invented by Taku Ogawa, Koki Yoshida, Daisuke Murakami, and Dai Hirose, upon which this patent application is based is hereby incorporated by reference.

BACKGROUND OF THE INVENTION

Field of the Invention

The present invention relates to an X-ray imaging apparatus.

Description of the Background Art

Conventionally, an X-ray imaging apparatus is known. Such an X-ray imaging apparatus is disclosed, for example, in JP 6115498.

JP 6115498 discloses an X-ray imaging apparatus provided with an X-ray tube for emitting X-rays to a subject, an X-ray detector, a collimator for adjusting the irradiation region of X-rays emitted from the X-ray tube, an image processing unit for performing image processing based on a detection signal detected by the X-ray detector, a detector for detecting a marker provided on a stent inserted into a blood vessel of a subject, and a control unit for controlling the collimator. In the X-ray imaging apparatus described in JP 6115498, the control unit highlights the stent in order to improve the visibility of the stent that is hard to be reflected in an X-ray image and to facilitate treatment. The control unit is configured to control the collimator so that the irradiation region of X-rays falls on the stent or the vicinity thereof based on the marker of the stent detected by the detector to narrow down the irradiation region of X-rays in the case of highlighting the stent.

SUMMARY OF THE INVENTION

In the X-ray imaging apparatus described in the above-mentioned Patent Document 1, in the case of highlighting the stent, the collimator is controlled so that the irradiation region of X-rays falls on the stent or the vicinity thereof based on the marker of the stent to narrow down the irradiation region of X-rays. Therefore, when detecting the stent marker, the irradiation region of X-rays is not narrowed down. In this case, since the irradiation region of X-rays is wide, the quality of the X-ray image becomes a relatively low state when the marker of the stent is detected due to the effects of the scattered light of X-rays or the like. For this reason, in some cases, the marker of the stent cannot be detected quickly from the X-ray image. In this instance, it is difficult to quickly narrow down the irradiation region of X-rays to quickly improve the X-ray image quality. Under the circumstances, it is desired to quickly narrow down the irradiation region of X-rays to quickly improve the quality of the X-ray image when highlighting the stent (predetermined target object).

The present invention has been made to solve the above-mentioned problems, and an object of the present invention is to provide an X-ray imaging apparatus capable of quickly narrowing down the irradiation region of X-rays to quickly improve the quality of an X-ray image when highlighting a predetermined target object.

An X-ray imaging apparatus according to one aspect of the present disclosure includes:

an X-ray irradiation unit configured to emits X-rays to a subject;

an X-ray detection unit configured to detect X-rays that have passed through the subject;

an image processing unit configured to generate an image based on a detection signal output from the X-ray detection unit;

an X-ray irradiation region adjustment unit including a shielding portion for shielding X-rays, the X-ray irradiation region adjustment unit being configured to adjust an X-ray irradiation region which is an irradiation region of X-rays emitted from the X-ray irradiation unit by moving the shielding portion; and a control unit configured to control the X-ray irradiation region adjustment unit to adjust the X-ray irradiation region based on a set region of interest in a case of a region of interest highlighting mode that highlights a predetermined target object in a region of interest set in an image generated by the image processing unit.

According to the present invention, a control unit is provided for controlling the X-ray irradiation region adjustment unit to adjust the X-ray irradiation region based on the set region of interest in the case of a region of interest highlighting mode that highlights a predetermined target object within a region of interest set in the image created by the image processing unit. With this, it is unnecessary to detect a characteristic point, such as, e.g., a marker of a predetermined target object, from the X-ray image captured prior to narrowing down the X-ray irradiation region and relatively low in image quality, so that the X-ray irradiation region can be quickly narrowed down based on the set region of interest. As a result, the quality of the X-ray image can be quickly improved. Further, since the X-ray irradiation region can be quickly narrowed down, the X-ray exposure of a subject can be reduced.

DESCRIPTION OF THE PREFERRED EMBODIMENT

Hereinafter, an embodiment in which the present invention is embodied will be described with reference to the drawings.

Embodiment

Figure 1:
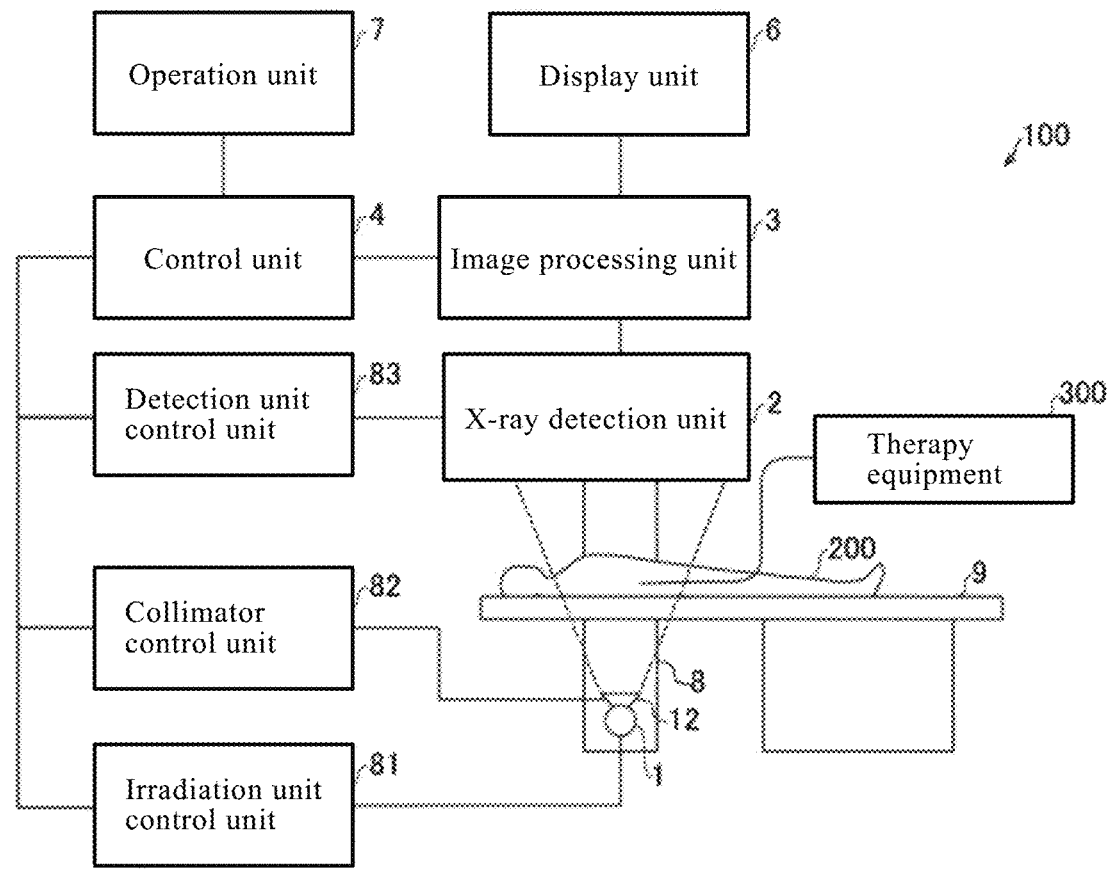
FIG. 1 is a block diagram showing an entire configuration of an X-ray imaging apparatus according to an embodiment of the present invention.

As shown in FIG. 1, an X-ray imaging apparatus 100 is provided with an image processing unit 3, a control unit 4, a display unit 6, an operation unit 7, a moving mechanism 8, and a top board 9. The moving mechanism 8 is provided with an X-ray irradiation unit 1 and an X-ray detection unit 2. The control unit 4 controls the X-ray irradiation unit 1, a collimator 12, and the X-ray detection unit 2 via an irradiation unit control unit 81, a collimator control unit 82, and a detection unit control unit 83.

The X-ray irradiation unit 1 emits X-rays to a subject 200 into which therapy equipment 300 is introduced. The X-ray detection unit 2 detects X-rays transmitted through the subject 200. The X-ray irradiation unit 1 and the X-ray detection unit 2 are arranged so as to face each other with the top board 9 on which the subject 200 is placed interposed therebetween. The X-ray irradiation unit 1 and the X-ray detection unit 2 are movably and rotatably supported by the moving mechanism 8. The top board 9 is horizontally movable by a top board drive unit (not shown). The control unit 4 moves the X-ray irradiation unit 1, the X-ray detection unit 2, and the top board 9 through the respective control units, the moving mechanism 8, and the top board drive unit so that a predetermined region of the subject 200 can be imaged. Note that the control unit includes the irradiation unit control unit 81, the collimator control unit 82, and the detection unit control unit 83. Also note that the therapy equipment 300 is an example of the "predetermined target object" recited in claims.

The X-ray irradiation unit 1 includes an X-ray tube (not shown). The X-ray tube is connected to a high voltage generator (not shown) and generates X-rays when a high voltage is applied thereto. The X-ray tube is arranged such that the X-ray emission direction faces the detection surface of the X-ray detection unit 2. The X-ray irradiation unit 1 is connected to the irradiation unit control unit 81. The irradiation unit control unit 81 controls the X-ray irradiation unit 1 to generate X-rays from the X-ray tube in accordance with preset imaging conditions, such as, e.g., tube voltages, tube currents, and time-intervals of X-ray emissions.

The collimator 12 is configured to shield a part of X-rays emitted from the X-ray tube to thereby enable the adjustment of the X-ray irradiation region 110. The collimator 12 is configured to be rotatable about the optical axis connecting the X-ray irradiation unit 1 and the X-ray detection unit 2. The collimator 12 is configured such that each leaf 120, which is composed of a plurality of plate-like members, is independently movable. The collimator 12 is configured such that the X-ray irradiation region 110 can be adjusted by shielding a part of the X-rays emitted from the X-ray tube. Note that the collimator 12 is an example of the "X-ray irradiation region adjustment unit" recited in claims, and the leaf 120 of the collimator 12 is an example of the "shielding portion" recited in claims.

The X-ray detection unit 2 detects the X-rays emitted from the X-ray irradiation unit 1 and transmitted through the subject 200 and outputs a detection signal corresponding to the detected X-ray intensity. The X-ray detection unit 2 is composed of, for example, an FPD (Flat Panel Detector). The X-ray detection unit 2 outputs an X-ray detection signal of a predetermined resolution to the image processing unit 3. The image processing unit 3 acquires the X-ray detection signal from the X-ray detection unit 2 and generates an image.

In the image processing unit 3, image processing is performed in real time during the image capturing. The image processing unit 3 is, for example, a computer configured to include a processor, such as, e.g., a CPU or a GPU (Graphics Processing Unit) and a storage unit, such as, a ROM and a RAM. That is, the image processing unit 3 is configured by making the processor execute an image processing program stored in the storage unit. The image processing unit 3 may be configured integrally with the control unit 4 by making the same hardware (CPU) as the control unit 4 execute an image processing program.

The image processing unit 3 is configured to generate an image based on a detection signal of X-rays that have passed through the subject 200 into which the therapy equipment 300 has been introduced. The image processing unit 3 generates an image in the form of a moving image based on a detection signal of the X-ray detection unit 2. That is, X-rays are intermittently emitted from the X-ray irradiation unit 1 to the subject 200 at predetermined time intervals, and the X-rays transmitted through the subject 200 are sequentially detected by the X-ray detection unit 2. The image processing unit 3 generates an image by imaging the detection signal sequentially output from the X-ray detection unit 2. The image processing unit 3 is also provided with a region of interest highlighting mode, which will be described later.

The control unit 4 is a computer including a CPU (Central Processing Unit), a ROM (Read Only Memory), a RAM (Random Access Memory), and the like. The control unit 4 functions as a control unit 4 for controlling each part of the X-ray imaging apparatus 100 by executing a predetermined control program by the CPU.

Further, the control unit 4 controls the image processing unit 3. The control unit 4 is configured to acquire, when the region of interest highlighting button is operated by an operator, information regarding switching of modes based on the operation contents to the region of interest highlighting button. The control unit 4 is configured to switch the mode of the image processing unit 3 to the region of interest highlighting mode by transmitting the information about the switching of the mode to the image processing unit 3.

The display unit 6 is, for example, a monitor, such as, e.g., a liquid crystal display, and can display, e.g., an image generated by the image processing unit 3. The control unit 4 is configured to perform control to display on the display unit 6 the image generated by the image processing unit 3 and the region of interest highlighting button for switching the mode of the image processing unit 3, which will be described later.

The operation unit 7 is configured such that an input of an operator relating to X-ray imaging can be accepted. The control unit 4 is configured to accept an input operation by an operator via the operation unit 7. Further, the control unit 4 detects the region of interest highlighting button switching operation by the operation unit 7 to switch the mode of the image processing unit 3, which will be described later.

The X-ray imaging apparatus 100 of this embodiment is configured such that images can be acquired by two methods, i.e., fluoroscopy and radiography. In the X-ray fluoroscopy, a radiation dose smaller than that of the X-ray radiography is emitted to the subject 200, so that the exposure dose of the subject 200 can be reduced, while an image (fluoroscopic image) low in image quality is acquired. On the other hand, in the X-ray imaging, an image (X-ray image) high in image quality to some extent is acquired.

Figure 2:
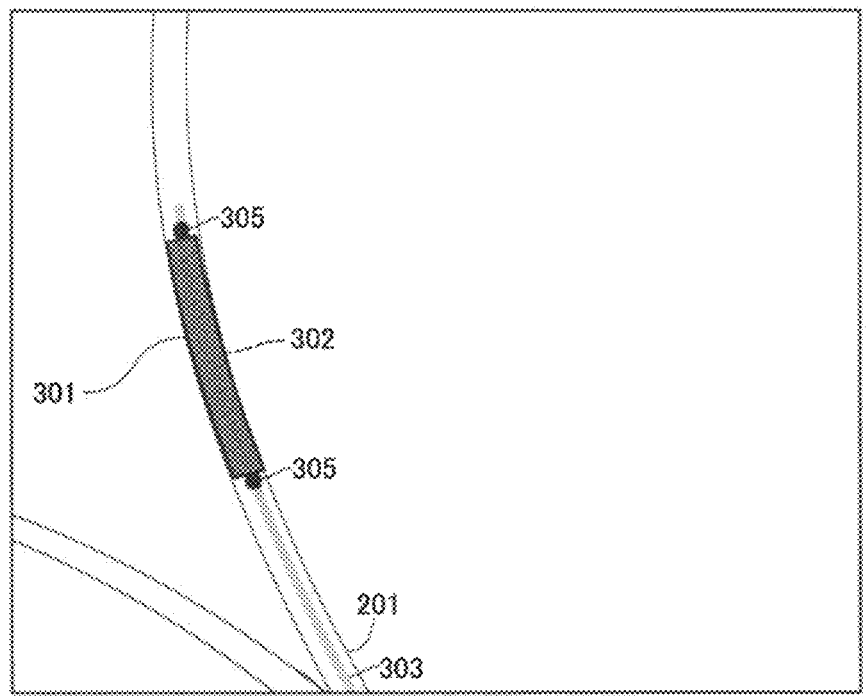
FIG. 2 is a diagram showing an example of a fluoroscopic image displayed on a display unit according to an embodiment of the present invention.

As shown in FIG. 2, the therapy equipment 300 includes a stent 301 inserted into a blood vessel 201 of the subject 200, a balloon 302 for inflating the stent 301, and a catheter 303. The stent 301 is a cylindrical member having a network structure formed of thin metals or the like, and allows X-rays to easily pass therethrough, so the stent is less likely to be reflected in an image. For this reason, the stent 301 or the balloon 302 is provided with a pair of markers 305 made of a material that is less radiolucent (or opaque) as marks. The pair of markers 305 is provided in the vicinity of both ends of the stent 301 so as to sandwich the stent 301 therebetween.

(Region of Interest Highlighting Mode)

In this embodiment, the image processing unit 3 is configured so that image processing of generating a composite image by superimposing a plurality of continuously generated images can be performed at the time of X-ray imaging. At the time of superimposing, for example, by superimposing (performing temporal integration) images of respective frames with reference to a characteristic point such as the marker 305 provided on the stent 301, a composite (integrated) image as a highlighted image highlighting the stent 301 is generated. The image processing unit 3 is configured to perform generation of a composite image every time an image is newly generated. With this, it is possible to display the generated composite image on the display unit 6 in real time as a moving image. Further, the image processing unit 3 is further provided with a region of interest highlighting mode that performs highlight imaging in which X-ray imaging is performed while highlighting a predetermined target object in a region of interest 402 set by setting a region of interest 402 (see FIG. 5), which will be described later.

(Setting Region of Interest in Region of Interest Highlighting Mode)

First, an operator performs X-ray fluoroscopy to confirm the positional variations of the marker 305 due to pulsation. The operator then operates the region of interest highlighting button displayed on the display unit 6. Based on the region of interest highlighting button being operated, the control unit 4 switches the mode of the image processing unit 3 to the region of interest highlighting mode, so that the region of interest highlighting mode is activated.

Figure 3:
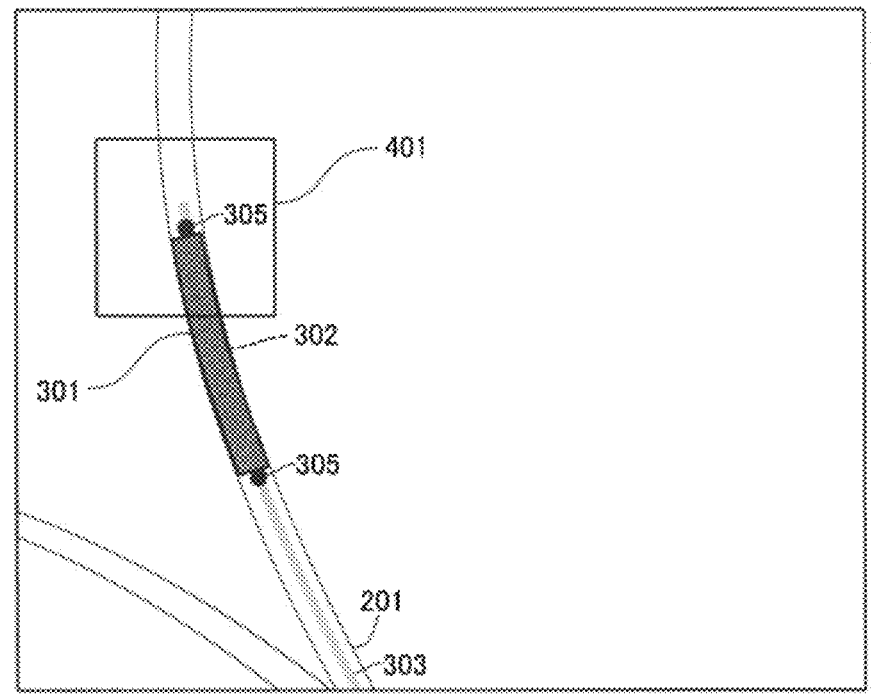
FIG. 3 is a diagram showing an example of one designated region displayed on the display unit at the time of a region of interest highlighting mode according to an embodiment of the present invention.

When the region of interest highlighting mode is activated, as shown in FIG. 3, the image processing unit 3 makes the display unit 6 display the designated region 401 and automatically reproduces the X-ray fluoroscopic image as a moving image. The designated region 401 is displayed so as to overlap with the moving image. When the region of interest highlighting button is operated once, a single designated region 401 is displayed on the display unit 6.

Figure 4:
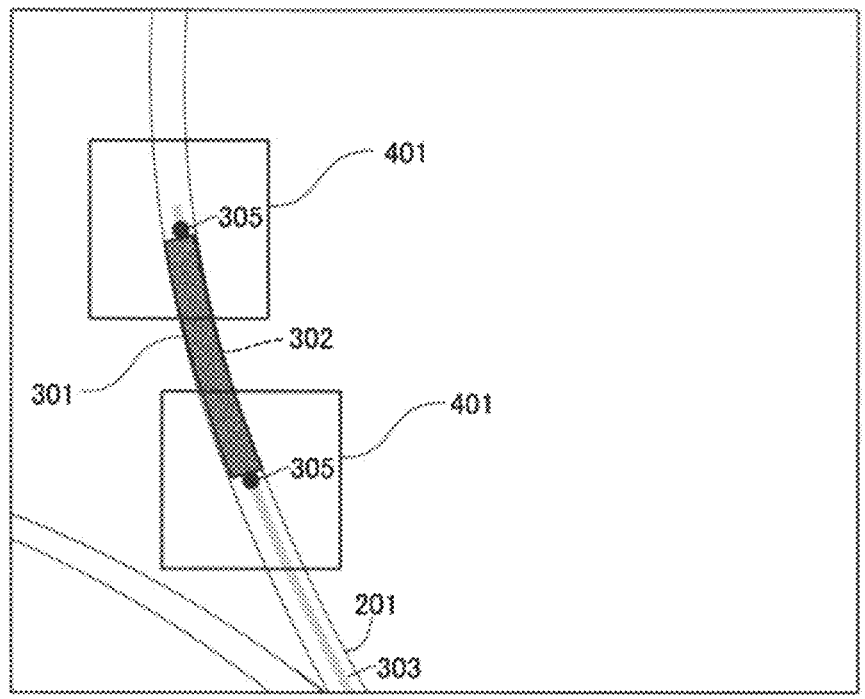
FIG. 4 is a diagram showing an example of two designated regions displayed on the display unit at the time of setting a region of interest in a region of interest highlighting mode according to an embodiment of the present invention.

When the region of interest highlighting button is operated again, one more designated region 401 is displayed, as shown in FIG. 4. The operator can adjust the position and size of the designated region 401 displayed on the display unit 6 by using the operation unit 7. With this, for example, the designated region 401 can be moved to a position of a target object such as the marker 305 of the stent 301. Although this embodiment exemplifies the use of two designated regions 401 in the region of interest setting, the number of the designated regions 401 used in the region of interest setting may be three or more, or only one designated region may be set. In the case of using only one designated region 401, the designated region 401 becomes a region of interest 402.

Figure 5:
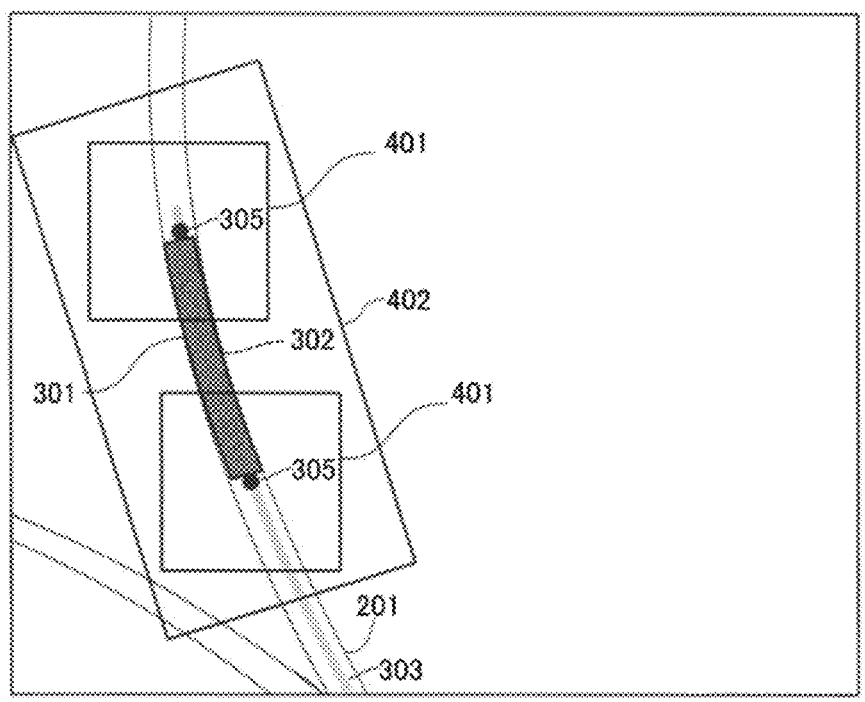
FIG. 5 is a diagram showing an example of a region of interest displayed on the display unit at the time of setting a region of interest in a region of interest highlighting mode according to an embodiment of the present invention.

Further, as shown in FIG. 5, the image processing unit 3 sets the region of interest 402 so that all the designated regions 401 set by the operator can be included in the region of interest 402. Note that in the case of using only one designated region 401, the designated region 401 itself becomes a region of interest 402. The region of interest 402 is set with certain margins, taking into account the effects of pulsations of, e.g., blood vessels 201 and organs.

(Control of Collimator)

Figure 6:
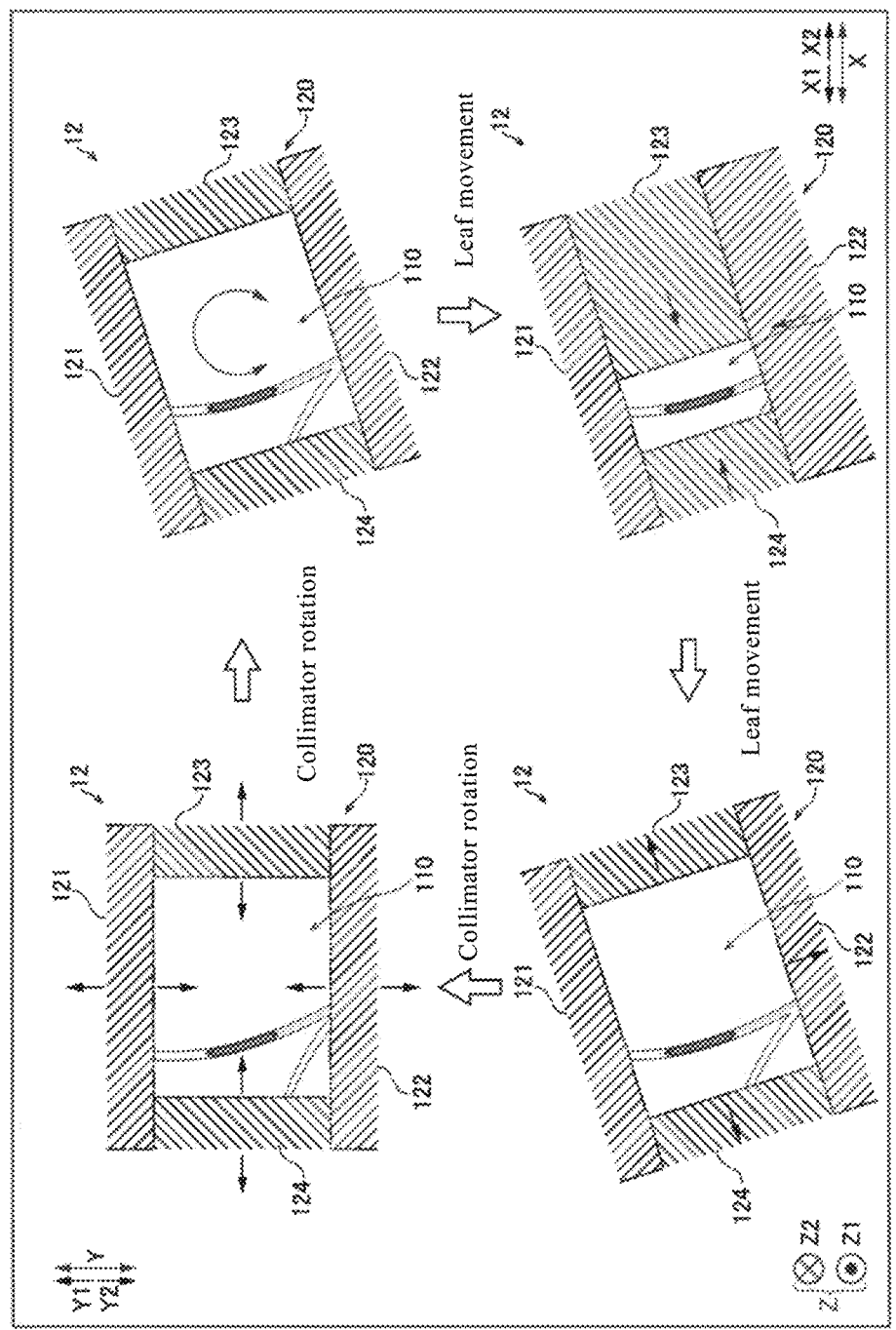
FIG. 6 is a schematic diagram for explaining the adjustment of the X-ray irradiation region by a collimator according to an embodiment of the present invention.

As shown in FIG. 6, the leaf 120 of the collimator 12 includes a first leaf portion 121 and a second leaf portion 122 arranged along the X-direction, and a third leaf portion 123 and a fourth leaf portion 124 arranged along the Y-direction. The plurality of leaf portions (first leaf portion 121, second leaf portion 122, third leaf portion 123, and fourth leaf portion 124) are controlled by the control unit 4 via the collimator control unit 82. It is configured such that the X-ray irradiation region 110 can be adjusted by individually moving the first leaf portion 121, the second leaf portion 122, third leaf portion 123, and the fourth leaf portion 124. The collimator 12 is configured to be rotatable about the Z-axis. Note that the first leaf portion 121, the second leaf portion 122, the third leaf portion 123, and the fourth leaf portion 124 are examples of the "shielding portion" recited in claims. The collimator 12 and the X-ray detection unit 2 are configured, in the region of interest highlighting mode, to be controlled by the control unit 4. The control unit 4 is configured to control the movements of the plurality of leaf portions and to control the rotations of the collimator 12 and the X-ray detection unit 2, based on the region of interest 402.

Figure 7:
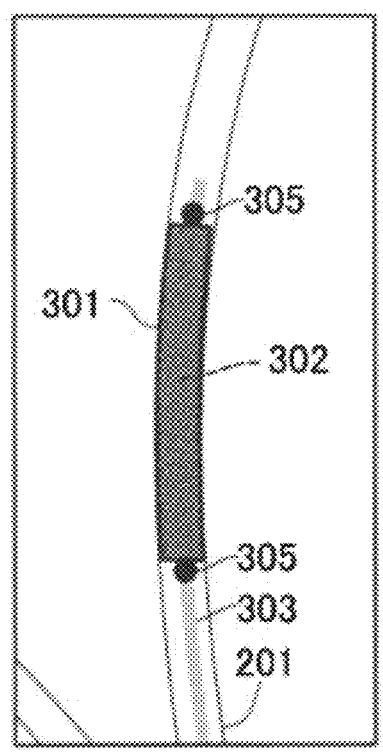
FIG. 7 is a diagram showing an example of a highlighted image displayed on the display unit at the time of highlight imaging a region of interest in the case of a highlighting mode by an embodiment of the present invention.

The control unit 4 controls the moving mechanism 8 to rotate the collimator 12 and the X-ray detection unit 2 along the set region of interest 402. Next, based on the set region of interest 402, the plurality of leaf portions is moved inward to narrow down the X-ray irradiation region 110. In the state in which the X-ray irradiation region 110 is narrowed down based on the set region of interest 402, by performing the highlight imaging, as shown in FIG. 7, the highlighted image of the set region of interest 402 is displayed on the display unit 6.

When the highlighting is completed, the control unit 4 moves the plurality of leaf portions outward to expand the X-ray irradiation region 110. Then, the control unit 4 controls the moving mechanism 8 to return to the state prior to the control by rotating the collimator 12 and the X-ray detection unit 2.

(Region of Interest Highlighting Mode Processing Flow)

Figure 8:
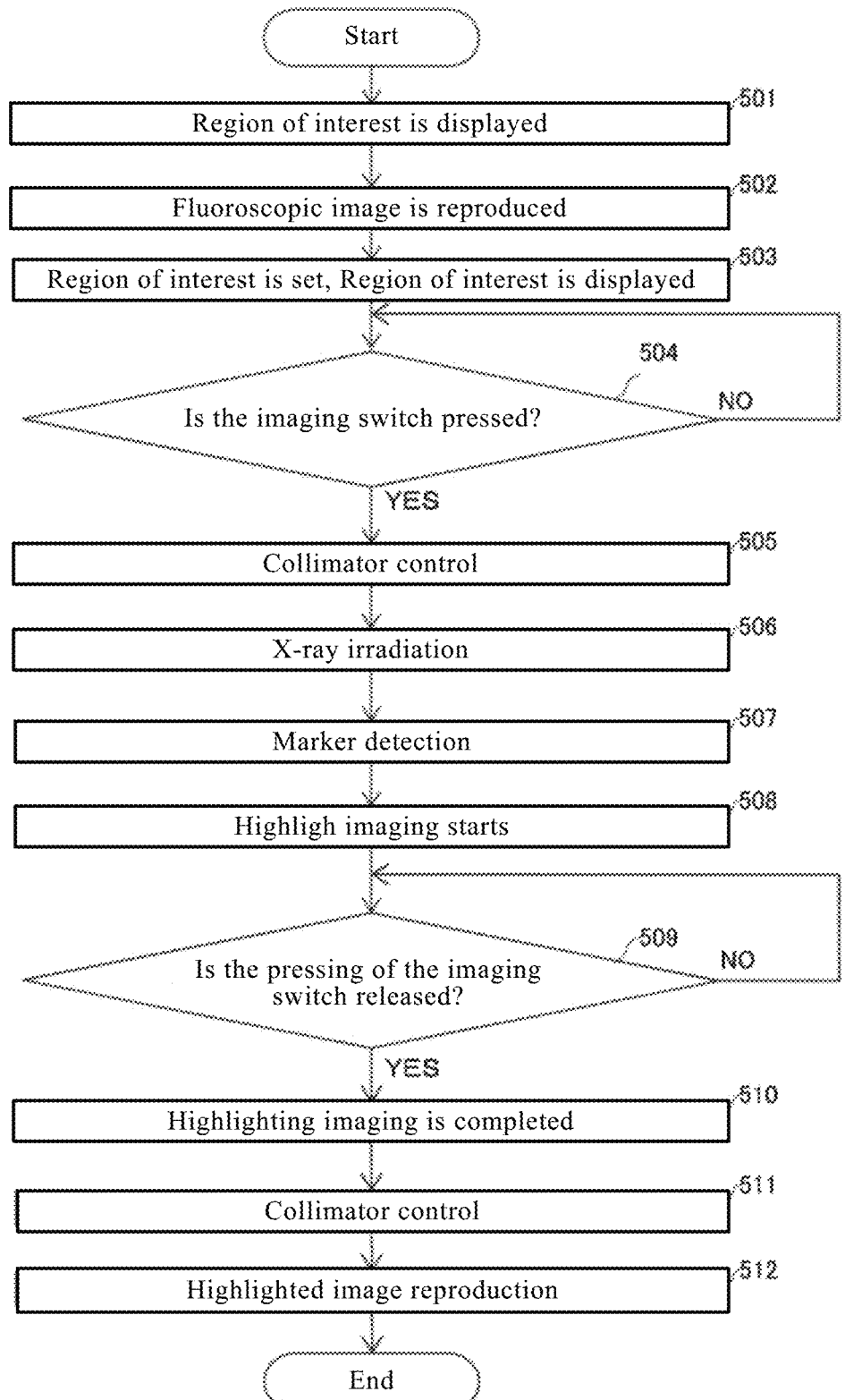
FIG. 8 is a flowchart for explaining a region of interest highlighting mode process according to an embodiment of the present invention.

Next, with reference to FIG. 8, the region of interest highlighting mode according to the X-ray imaging apparatus 100 of this embodiment will be described with reference to a flowchart. The region of interest highlighting mode processing is performed by the control unit 4.

In Step 501, the designated region 401 is displayed on the display unit 6. After the designated region 401 is displayed, the process proceeds to Step 502.

In Step 502, a fluoroscopic image is reproduced on the display unit 6. The reproduced fluoroscopic image is a moving image of the X-ray fluoroscopy performed prior to the region of interest highlighting mode. When the fluoroscopic image is reproduced, the process proceeds to Step 503 of X-ray imaging.

In Step 503, the region of interest 402 is set, and the set region of interest 402 is displayed on the display unit 6. Upon completion of the display of the region of interest 402 set in the display unit 6, the process proceeds to Step 504.

In Step 504, when it is determined that the imaging switch is pressed, the process proceeds to Step 505.

On the other hand, in Step 504, when it is determined that the imaging switch has not been pressed, the determination of Step 504 is repeated until it is determined that the imaging switch is pressed.

In Step 505, the control of the collimator 12 is performed based on the set region of interest 402. When rotating the collimator 12, the X-ray detection unit 2 is rotated in the same manner. When the control of the collimator 12 is completed, the process proceeds to Step 506.

In Step 506, the X-rays are irradiated and the process proceeds to Step 507.

In Step 507, the marker 305 within the set region of interest 402 is detected, and the process proceeds to Step 508. When no marker 305 is detected within the set region of interest 402, normal X-ray imaging without performing highlighting is performed.

In Step 508, highlight imaging is started. The image processing unit 3 performs highlighting on the captured X-ray image to perform highlight imaging. Then, when highlight imaging is initiated, the process proceeds to Step 509.

When it is determined in Step 509 that the pressing of the imaging switch is released, the process proceeds to Step 510.

On the other hand, when it is determined in Step 509 that the imaging switch is being continuously pressed, the determination of Step 509 is repeated until it is determined that the pressing of the imaging switch is released.

In Step 510, the highlight imaging is completed. Then, when the highlight imaging is completed, the process proceeds to Step 511.

In Step 511, the control of the collimator 12 is performed. The collimator 12 is controlled to return to the previous state prior to Step 505. When the collimator 12 is rotated, the X-ray detection unit 2 is rotated in the same manner. Upon completion of the control of the collimator 12, the process proceeds to Step 512.

In Step 512, the highlighted images captured between Step 507 and Step 509 are reproduced.

Effects of Embodiment

In this embodiment, the following effects can be obtained.

In this embodiment, the X-ray imaging apparatus 100 is provided with the control unit 4 that controls the collimator 12 (X-ray irradiation region adjustment unit) to adjust the X-ray irradiation region 110 based on the set region of interest 402 in the case of the region of interest highlighting mode that highlights the therapy equipment 300 (predetermined target object) within the region of interest 402 set in the image created by the image processing unit 3. With this, there is no need to detect a characteristic point such as a marker 305 of the therapy equipment 300 (predetermined target object) from the X-ray image in which the image is relatively low in quality prior to the X-ray irradiation region 110 being narrowed down, so that the X-ray irradiation region 110 can be quickly narrowed down based on the set region of interest 402. As a result, the quality of the X-ray image can be quickly improved. In addition, since the X-ray irradiation region 110 can be quickly narrowed down, the X-ray exposure of the subject 200 can be reduced.

In addition, in this embodiment, the control unit 4 is configured to perform control to detect the therapy equipment 300 (predetermined target object) within the region of interest 402 or the marker 305 provided on the therapy equipment 300 (predetermined target object) after performing the control of the collimator 12 (X-ray irradiation region adjustment unit) so as to adjust the X-ray irradiation region 110. With this, the marker 305 of the therapy equipment 300 (predetermined target object) can be detected from the X-ray image in which the X-ray irradiation region 110 has been narrowed down and the image quality has been improved. In addition, the marker 305 provided on the therapy equipment 300 (predetermined target object) can be detected from the X-ray image in which the X-ray irradiation region 110 has been narrowed down and the range has been narrowed down. As a result of these, the marker 305 can be easily and quickly detected within the X-ray image.

In addition, in this embodiment, the control unit 4 is configured to perform the control of the collimator 12 (X-ray irradiation region adjustment unit) so as to narrow down the X-ray irradiation region 110 based on the set region of interest 402 in the case of the region of interest highlighting mode. With this, the scattered X-rays from the outside region of interest 402 can be removed, so that the quality of X-ray image in the region of interest 402 can be improved.

In addition, in this embodiment, the control unit 4 is configured to control such that, in the case of the region of interest highlighting mode, highlighting is performed by the image processing unit 3 after the collimator 12 (X-ray irradiation region adjustment unit) is controlled. As a result, since the X-ray irradiation region 110 is adjusted at the start of highlighting, it is possible to display an X-ray image in which the image quality is high immediately after the start of highlighting.

Further, in this embodiment, the leaf 120 (shielding portion) of the collimator 12 includes a plurality of leaf portions (shielding members) each independently movable, i.e., the first leaf portion 121, the second leaf portion 122, the third leaf portion 123, and the fourth leaf portion 12. The collimator 12 (X-ray irradiation region adjustment unit) and the X-ray detection unit 2 are configured to be rotatable about the optical axis connecting the X-ray irradiation unit 1 and the X-ray detection unit 2. The control unit 4 is configured to perform, based on the region of interest 402, the control to move the plurality of leaf portions (shielding portion materials), i.e., the first leaf portion 121, the second leaf portion 122, the third leaf portion 123, and the fourth leaf portion 124 and the control to rotate the collimator 12 (X-ray irradiation region adjustment unit) and the X-ray detection unit 2. With this, even if the center position of the X-ray irradiation region 110 is not aligned with the therapy equipment 300 (predetermined target object) in advance, the X-ray irradiation region 110 can be adjusted so that the therapy equipment 300 (predetermined target object) is reflected by moving the plurality of leaf portions (shielding portions), i.e., the first leaf portion 121, the second leaf portion 122, the third leaf portion 123, and the fourth leaf portion 124.

In addition, in this embodiment, the control unit 4 is configured to perform the control of the collimator 12 (X-ray irradiation region adjustment unit) so as to expand the X-ray irradiation region 110 after highlighting is completed in the case of the region of interest highlighting mode. With this, since the X-ray irradiation region 110 is expanded after the highlighting is completed, it is possible to confirm a region larger than that in the case of highlighting after the highlight is completed. As a result, when continuously imaging another portion, the next portion to be imaged can be easily searched, so that the operability can be improved.

Also, in this embodiment, the image processing unit 3 is configured to set the region of interest 402 so that all of one or a plurality of designated regions 401 set by the operator in the image fit therein. With this, since the region of interest 402 can be set by the plurality of designated regions 401, it is possible to set the region of interest 402 in more detail than when it is set by only one designated region 401.

Further, in this embodiment, the therapy equipment 300 (predetermined target object) is therapy equipment 300 inserted into the subject 200. With this, when highlighting the therapy equipment 300 such as the stent 301 inserted into the subject 200, the X-ray irradiation region 110 can be quickly narrowed down and the quality of X-ray image can be quickly improved.

Modified Embodiment

It should be noted that the embodiment disclosed herein is to be considered in all respects as illustrative and not restrictive. The scope of the present invention is indicated by claims rather than by the embodiment described above, and all modifications within the meaning and range equivalent to those of claims are included.

For example, the above embodiment shows an example in which the collimator 12 (X-ray irradiation region adjustment unit) is controlled prior to starting the highlight imaging so as to adjust the X-ray irradiation region 110, but the present invention is not limited thereto. In the present invention, the X-ray irradiation region adjustment unit may be controlled after the highlight imaging is started so as to adjust the X-ray irradiation region.

Further, in the above embodiment, an example is shown in which highlight imaging is performed after the marker 305 is detected in the case of the region of interest highlighting mode, but the present invention is not limited to this. The present invention may be configured to perform highlight imaging without detecting an marker.

In the above embodiment, an example is shown in which a plurality of leaf portions (shielding members) of the collimator 12 (X-ray irradiation region adjustment unit) is independently movable, but the present invention is not limited thereto. In the present invention, the X-ray irradiation region adjustment unit may be configured such that the shielding portions move in an interlocking manner.

In the above embodiment, an example is shown in which the control of the collimator 12 (X-ray irradiation region adjustment unit) is performed so as to expand the X-ray irradiation region 110 after the highlight imaging is completed, but the present invention is not limited to this. In the present invention, the X-ray irradiation region adjustment unit may be controlled so as to expand the X-ray irradiation region 110 when the region of interest highlighting mode is completed.

In the above embodiment, an example is shown in which the collimator 12 (X-ray irradiation region adjustment unit) is controlled based on the set region of interest 402 and highlight imaging is performed only in the region of interest highlighting mode of performing highlight imaging, but the present invention is not limited to this. The present invention may further include, in addition to the region of interest highlighting mode, an imaging mode in which the X-ray irradiation region adjustment unit is controlled and highlight imaging mode is performed based on a marker provided on a predetermined target object.

Further, in the above embodiment, for convenience of explanation, the description is made using a driven type flowchart in which processing of the X-ray imaging apparatus 100 of the present invention is performed in order along the processing flow, but the present invention is not limited to this. In the present invention, the processing operation may be performed by the event-driven processing that executes processing on an event-by-event basis. In this case, the operation may be performed in a complete event-driven type or in a combination of event-driven and flow-driven.

Aspects

It will be understood by those skilled in the art that the above described exemplary embodiments are concrete examples of the following aspects.

(Item 1)
An X-ray imaging apparatus includes:
an X-ray irradiation unit configured to emits X-rays to a subject;
an X-ray detection unit configured to detect X-rays that have passed through the subject;
an image processing unit configured to generate an image based on a detection signal output from the X-ray detection unit;
an X-ray irradiation region adjustment unit including a shielding portion for shielding X-rays, the X-ray irradiation region adjustment unit being configured to adjust an X-ray irradiation region which is an irradiation region of X-rays emitted from the X-ray irradiation unit by moving the shielding portion; and
a control unit configured to control the X-ray irradiation region adjustment unit to adjust the X-ray irradiation region based on a set region of interest in a case of a region of interest highlighting mode that highlights a predetermined target object in a region of interest set in an image generated by the image processing unit.

(Item 2)
The X-ray imaging apparatus as recited in the aforementioned Item 1,
wherein the control unit is configured to control the X-ray irradiation region adjustment unit so as to adjust the X-ray irradiation region, and then to detect the predetermined target object or a marker provided on the predetermined target object in the region of interest (Item 3)
The X-ray imaging apparatus as recited in the aforementioned Item 2,
wherein the control unit is configured to control the X-ray irradiation region adjustment unit so as to narrow down the X-ray irradiation region based on the set region of interest in a case of the region of interest highlighting mode.

(Item 4)
The X-ray imaging apparatus as recited in the aforementioned Item 3,
wherein, in a case of the region of interest highlighting mode, the control unit is configured to control highlighting by the image processing unit after controlling the X-ray irradiation region adjustment unit.

Item 5
The X-ray imaging apparatus as recited in any one of the aforementioned Items 1 to 4, wherein the shielding portion includes a plurality of shielding members each independently movable, wherein the X-ray irradiation region adjustment unit and the X-ray detection unit are configured to be rotatable about an optical axis connecting the X-ray irradiation unit and the X-ray detection unit, and wherein the control unit is configured to control movements of the plurality of shielding members and to control rotations of the X-ray irradiation region adjustment unit and the X-ray detection unit based on the region of interest.

(Item 6)

The X-ray imaging apparatus as recited in the aforementioned Item 3 or 4, wherein the control unit is configured to control the X-ray irradiation region adjustment unit so as to expand the X-ray irradiation region after highlighting is completed in a case of the region of interest highlighting mode.

(Item 7)

The X-ray imaging apparatus as recited in the aforementioned Item 1, wherein the image processing unit is configured to set the region of interest such that all of one or a plurality of designated regions set by an operator fit in the region of interest.

(Item 8)

The X-ray imaging apparatus as recited in the aforementioned Item 2, wherein the predetermined target object is therapy equipment to be inserted into the subject.

The invention claimed is:

1. An X-ray imaging apparatus comprising:
an X-ray irradiation unit configured to emits X-rays to a subject;
an X-ray detection unit configured to detect X-rays that have passed through the subject;
an image processing unit configured to generate an X-ray image based on a detection signal output from the X-ray detection unit;
an X-ray irradiation region adjustment unit including a shielding portion for shielding X-rays, the X-ray irradiation region adjustment unit being configured to adjust an X-ray irradiation region which is an irradiation region of X-rays emitted from the X-ray irradiation unit by moving the shielding portion; and
a control unit configured to control the X-ray irradiation region adjustment unit to adjust the X-ray irradiation region based on a region of interest preset on the basis of a fluoroscopic image which is generated by a radiation smaller than that of the X-ray image before imaging the X-ray image in a case of a region of interest highlighting mode that highlights a predetermined target object in the region of interest set in the X-ray image generated by the image processing unit.

2. The X-ray imaging apparatus as recited in claim 1, wherein the control unit is configured to control the X-ray irradiation region adjustment unit so as to adjust the X-ray irradiation region, and then to detect the predetermined target object or a marker provided on the predetermined target object in the region of interest.

3. The X-ray imaging apparatus as recited in claim 2, wherein the control unit is configured to control the X-ray irradiation region adjustment unit so as to narrow down the X-ray irradiation region based on the region of interest preset before imaging the X-ray image in the case of the region of interest highlighting mode.

4. The X-ray imaging apparatus as recited in claim 3, wherein, in a case of the region of interest highlighting mode, the control unit is configured to control highlighting by the image processing unit after controlling the X-ray irradiation region adjustment unit.

5. The X-ray imaging apparatus as recited in claim 3, wherein the control unit is configured to control the X-ray irradiation region adjustment unit so as to expand the X-ray irradiation region after highlighting is completed in a case of the region of interest highlighting mode.

6. The X-ray imaging apparatus as recited in claim 2, wherein the predetermined target object is therapy equipment to be inserted into the subject.

7. The X-ray imaging apparatus as recited in claim 1, wherein the shielding portion includes a plurality of shielding members each independently movable, wherein the X-ray irradiation region adjustment unit and the X-ray detection unit are configured to be rotatable about an optical axis connecting the X-ray irradiation unit and the X-ray detection unit, and wherein the control unit is configured to control movements of the plurality of shielding members and to control rotations of the X-ray irradiation region adjustment unit and the X-ray detection unit based on the region of interest.

8. The X-ray imaging apparatus as recited in claim 1, wherein the image processing unit is configured to set the region of interest such that all of one or a plurality of designated regions set by an operator fit in the region of interest.

9. An X-ray imaging method comprising:
a first irradiation starting step of starting emission of X-rays to a subject;
a first X-ray image acquisition step of acquiring a first X-ray image based on the X-rays emitted in the first irradiation step and passed through the subject;
a first irradiation stopping step of stopping emission of X-rays to the subject started in the first irradiation starting step;
a region of interest setting step of setting a region of interest in the first X-ray image;
a shielding portion controlling step of controlling a shielding portion for shielding X-rays based on the region of interest set in the region of interest setting step;
a second irradiation starting step of starting emission of X-rays to the subject after controlling the shielding portion in the shielding portion controlling step;
a second X-ray image acquisition step of sequentially acquiring a second X-ray image based on the X-rays emitted in the second irradiation step and passed through the subject; and
a highlighting step of highlighting a predetermined target object in the second X-ray image that is sequentially acquired.

* * * * *